United States Patent
Gami et al.

(10) Patent No.: US 10,451,340 B2
(45) Date of Patent: Oct. 22, 2019

(54) LOW TEMPERATURE STORAGE SYSTEMS AND RELATED METHODS

(71) Applicant: CooperSurgical, Inc., Trumbull, CT (US)

(72) Inventors: Aabha Bharat Gami, Weehawken, NJ (US); Matthew Benjamin Kandl, Cranford, NJ (US); Paul Landis Moyer, Long Valley, NJ (US); Rohit Suryadevara, Troy, NY (US)

(73) Assignee: CooperSurgical, Inc., Trumbull, CT (US)

( * ) Notice: Subject to any disclaimer, the term of this patent is extended or adjusted under 35 U.S.C. 154(b) by 57 days.

(21) Appl. No.: 15/840,268

(22) Filed: Dec. 13, 2017

(65) Prior Publication Data

US 2019/0178569 A1   Jun. 13, 2019

(51) Int. Cl.
*F25D 29/00*   (2006.01)
*F25D 25/00*   (2006.01)

(52) U.S. Cl.
CPC ......... *F25D 29/001* (2013.01); *F25D 25/005* (2013.01); *F25D 29/008* (2013.01); *F25D 2325/00* (2013.01); *F25D 2700/00* (2013.01)

(58) Field of Classification Search
CPC .... A01N 1/0257; A01N 1/0268; F25D 29/001
See application file for complete search history.

(56) References Cited

U.S. PATENT DOCUMENTS

| 2004/0074119 A1* | 4/2004 | Kim .......................... G09F 3/00 40/312 |
| 2013/0219948 A1* | 8/2013 | Aurekoski ......... B64D 11/0007 62/457.1 |
| 2013/0232998 A1* | 9/2013 | Ward ..................... B21D 53/00 62/51.1 |

(Continued)

FOREIGN PATENT DOCUMENTS

| CN | 205 357 945 | 7/2016 | ............... A01N 1/02 |
| GB | 2 523 252 | 8/2015 | ............... B60P 3/20 |

OTHER PUBLICATIONS

Cryo Bio System / Assisted Reproductive Technologies / Accessories, CBS Visotubes and goblets downloaded on Dec. 18, 2017, https://www.cryobiosystem-imv.com/en/assisted-reproductive-technologies/accessories/26-cbs-visotubes-and-goblets.html.

(Continued)

*Primary Examiner* — David M. Gray
*Assistant Examiner* — Andrew V Do
(74) *Attorney, Agent, or Firm* — Fish & Ricahrdson P.C.

(57) ABSTRACT

A low temperature storage system includes a cabinet housing and a drawer that is slidable in and out of the cabinet housing. The drawer includes an interior wall and an exterior wall defining an insular space therebetween and a support grid disposed within an interior region defined by the interior wall of the drawer. The support grid defines multiple receptacles arranged in a matrix configuration and respectively sized to receive a storage carrier. The drawer further includes first markings and second markings printed on the (Continued)

drawer in a manner such that any one of the first markings and any one of the second markings together correspond to one of the multiple receptacles arranged in the matrix configuration.

32 Claims, 8 Drawing Sheets

(56) References Cited

U.S. PATENT DOCUMENTS

2013/0320832 A1* 12/2013 Ward .................. B01L 9/00
312/408
2014/0157798 A1   6/2014 Jimenez-Rios et al.

OTHER PUBLICATIONS

International Search Report and Written Opinion for International Application No. PCT/US2018/064183 dated Feb. 12, 2019.

* cited by examiner

LOW TEMPERATURE STORAGE SYSTEMS AND RELATED METHODS

TECHNICAL FIELD

This disclosure relates to low temperature storage systems and related methods of storing specimens.

BACKGROUND

Low temperature storage systems, such as cryostorage systems, are used in the field of assisted reproductive technology (ART) to store and preserve living reproductive specimens over extended periods of time by maintaining the specimens at sub-zero temperatures within a low temperature substance. For example, a cryostorage system can house and support specimens that are undergoing or have undergone vitrification, which is the rapid transition of a substance from a liquid phase to a solid phase (e.g., glass) without the formation of ice crystals within cells of the specimen.

SUMMARY

In general, this disclosure relates to low temperature storage systems (e.g., cryostorage systems) and related methods of storing specimens in the storage systems. Such storage systems can be used for preserving living specimens in a viable state over a prolonged period of time.

In one aspect, a low temperature storage system includes a cabinet housing and a drawer that is slidable in and out of the cabinet housing. The drawer includes an interior wall and an exterior wall defining an insular space therebetween and a support grid disposed within an interior region defined by the interior wall of the drawer. The support grid defines multiple receptacles arranged in a matrix configuration and respectively sized to receive a storage carrier. The drawer further includes first markings and second markings printed on the drawer in a manner such that any one of the first markings and any one of the second markings together correspond to one of the multiple receptacles arranged in the matrix configuration.

Embodiments may provide one or more of the following features.

In some embodiments, the first and second markings include alphanumeric labels.

In certain embodiments, the first and second markings are printed on the support grid.

In some embodiments, the first and second markings are printed on the interior wall.

In certain embodiments, the drawer further includes shaded columnar marks disposed along the interior wall.

In some embodiments, the multiple receptacles include 1200 to 1500 receptacles.

In certain embodiments, each of the multiple receptacles has a length of about 1.1 cm to about 1.2 cm and a width of about 1.1 cm to about 1.2 cm.

In some embodiments, the multiple receptacles have a rectangular cross-sectional shape.

In certain embodiments, the interior and exterior walls include titanium.

In some embodiments, the insular space includes a vacuum pressure.

In certain embodiments, the drawer is configured to hold a fluid having a temperature of about −196° C. or less within the interior region.

In some embodiments, the low temperature storage system further includes a level sensor that is configured to detect a level of the fluid.

In certain embodiments, the low temperature storage system further includes an alarm that is configured to emit an alert when a level of the fluid falls below a threshold level.

In some embodiments, the drawer further includes a lid configured to close the interior region.

In certain embodiments, the lid includes a cover defining an opening through which a fluid can be delivered to the interior region and a cap configured to close the opening.

In some embodiments, the drawer is a first drawer, and the low temperature storage system further includes a second drawer that is slidable in and out of the cabinet housing.

In certain embodiments, the first and second drawers are arranged in a stacked vertical configuration within the cabinet housing.

In some embodiments, the low temperature storage system further includes the storage carrier.

In certain embodiments, the storage carrier includes a rectangular receptacle sized to fit within each of the multiple receptacles of the support grid and to carry multiple cryopreservation devices.

In some embodiments, the storage carrier includes a handle that extends from the rectangular receptacle.

In another aspect, a low temperature storage container includes an interior wall and an exterior wall defining an insular space therebetween and a support grid disposed within an interior region defined by the interior wall. The support grid defines multiple receptacles arranged in a matrix configuration and respectively sized to receive a storage carrier. The low temperature storage container further includes first markings and second markings printed on the low temperature storage container in a manner such that any one of the first markings and any one of the second markings together correspond to one of the multiple receptacles arranged in the matrix configuration.

Embodiments may provide one or more of the following features.

In some embodiments, the first and second markings comprise alphanumeric labels.

In certain embodiments, the first and second markings are printed on the support grid.

In some embodiments, the first and second markings are printed on the interior wall.

In certain embodiments, the low temperature storage container further includes shaded columnar marks disposed along the interior wall.

In some embodiments, the multiple receptacles include 600 to 800 receptacles.

In certain embodiments, each of the multiple receptacles has a length of about 1.1 cm to about 1.2 cm and a width of about 1.1 cm to about 1.2 cm.

In some embodiments, the multiple receptacles have a rectangular cross-sectional shape.

In certain embodiments, the interior and exterior walls include titanium.

In certain embodiments, the insular space includes a vacuum pressure.

In some embodiments, the low temperature storage container further includes a lid configured to close the interior region.

In certain embodiments, the lid includes a cover defining an opening through which a fluid can be delivered to the interior region and a cap configured to close the opening.

In some embodiments, the low temperature storage container is configured to hold a fluid having a temperature of about −196° C. or less within the interior region.

The low temperature storage system provides several advantages with respect to conventional low temperature specimen storage apparatuses. For example, the storage system provides a storage capacity that scales with a number of drawers arranged in a stacked configuration within a cabinet housing of the storage system, such that the storage system optimally uses vertical space while minimizing horizontal space. Therefore, a capacity of the storage system to store cryostorage carriers (e.g., the number of drawers multiplied by a number of storage receptacles included within each drawer) is not limited by a footprint of the storage system. In this regard, a storage capacity of the storage system can be about 5-10 times greater than that of other specimen storage apparatuses that have similar footprints. Furthermore, the rectangular (e.g., square) shape of the footprint of the cabinet housing increases (e.g., maximizes) a use of floor space for a given footprint length and width. Additionally, the multi-well design of a support grid of the storage system (e.g., including the storage receptacles, alphanumeric labels, and shaded columns) provides a two-dimensional, organized manner of storing the cryostorage carriers in an easy-to-use and easy-to-identify manner that reduces the risk of patient or sample misidentification.

DETAILED DESCRIPTION

Figure 1:
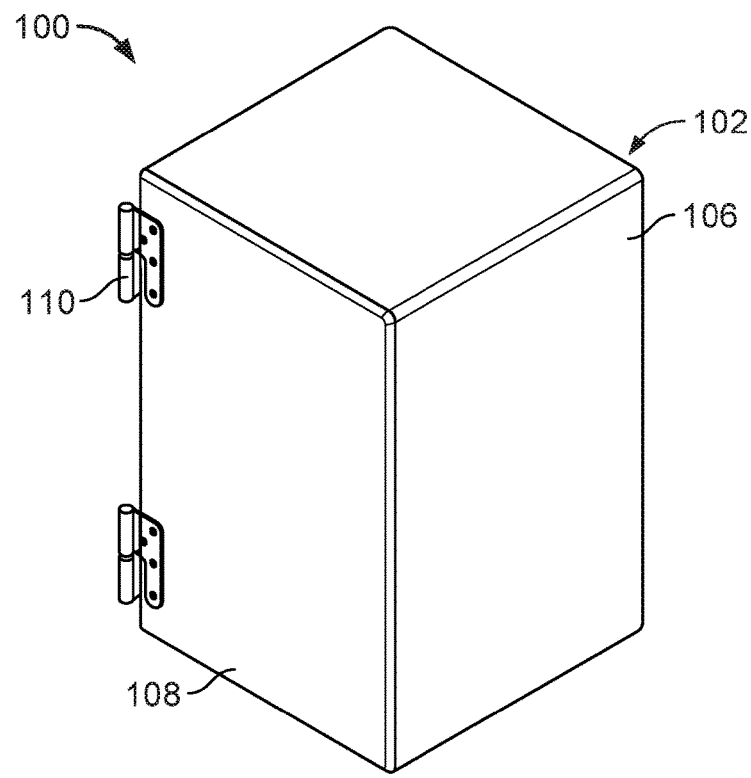
FIG. 1 is a perspective view of a low temperature storage system with a door of a cabinet housing in a closed position.
Figure 2:
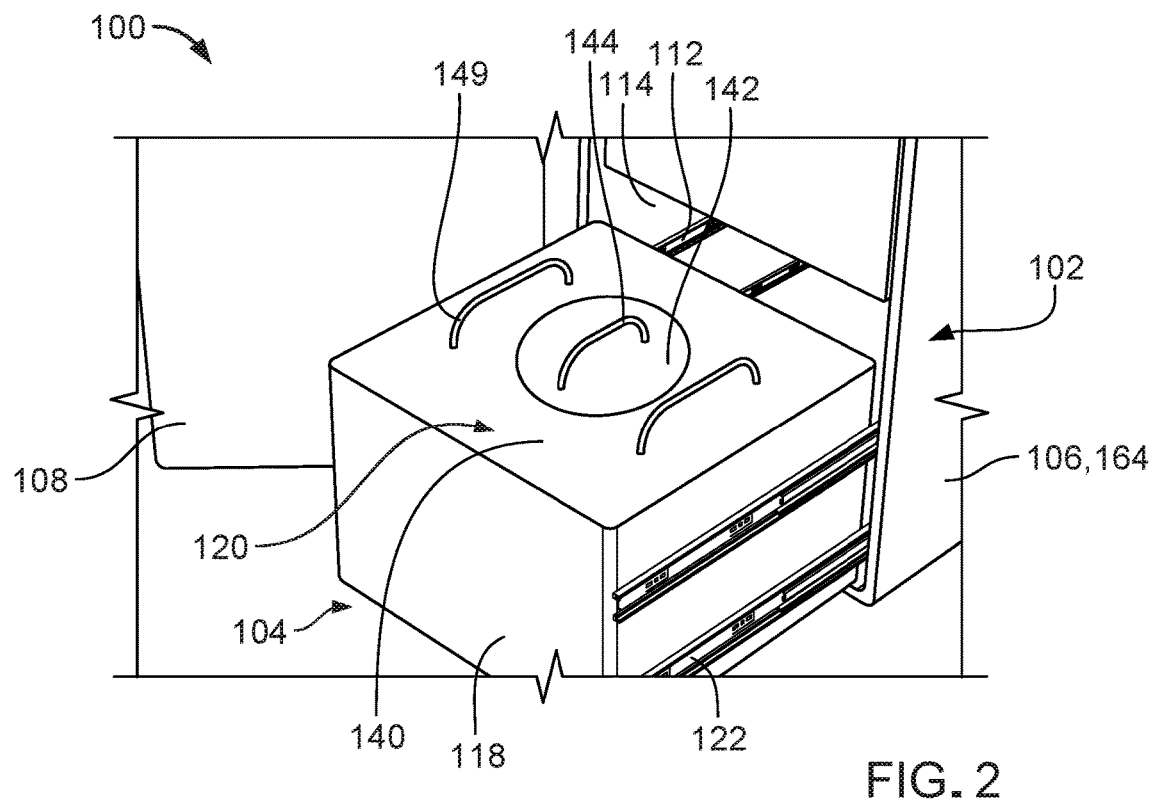
FIG. 2 is a perspective view of a portion of the storage system of FIG. 1, with the door open and a drawer slid out from the cabinet housing.
Figure 3:
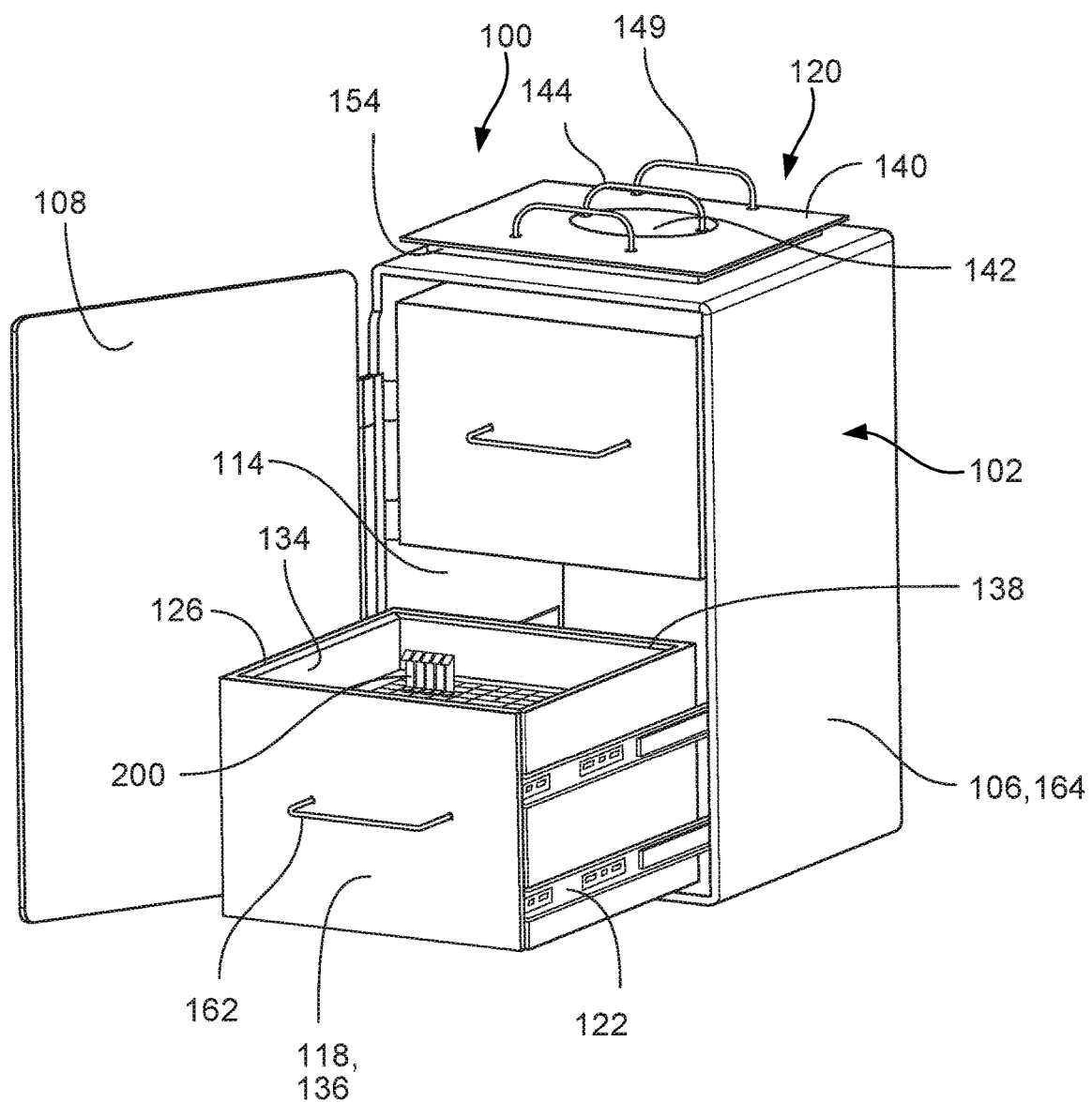
FIG. 3 is a perspective view of the storage system of FIG. 2, with a lid removed from the drawer.

FIGS. 1-3 illustrate various different views and configurations of a storage system 100 that can be used to store specimens (e.g., biological specimens) in a low temperature fluid substance. In particular, the storage system 100 is a cryostorage system that is configured to preserve the specimens in a viable and vitrified state within the low temperature substance until the specimens are desired for use (e.g., for a period of up to about 40 years). A specimen may be a single cell, a collection of free (e.g., unattached) cells, or a collection of attached cells (e.g., a multicellular tissue). Example specimens include reproductive specimens (e.g., oocytes, zygotes, embryos, blastocysts, and gastrulae) and other, non-reproductive specimens (e.g., T-cells and blood cells). The specimens may be mammalian samples or non-mammalian samples. The low temperature substance (e.g., liquid nitrogen, cryogenic plasma, or liquid helium) typically has a temperature of about −80° C. to about −296° C. (e.g., about −196° C.) and maintains the specimen in a vitrified state.

The storage system 100 includes a cabinet housing 102 and two drawers 104 that are located within the cabinet housing 102. The storage system 100 also includes a sensor system 116 that is integrated with the cabinet housing 102 and the drawers 104, as will be discussed in more detail below with respect to FIG. 9. The cabinet housing 102 includes a support frame 106 to which the drawers 104 are connected and a door 108 that is movable relative to the support frame 106 to permit the drawers 104 to be opened (refer to FIGS. 2 and 3) and closed (refer to FIG. 1). The door 108 is attached to the support frame 106 via multiple hinges 110. The cabinet housing 102 may include a latch or a magnetic member by which the door 108 can be secured to the support frame 106. The cabinet housing 102 is formed from a double wall that is defined by an interior surface 114 and an exterior surface 164. Referring particularly to FIG. 3, the support frame 106 includes multiple tracks 112 disposed along the interior surface 114 that engage and position the drawers 104. The support frame 106 includes four tracks 112 for each drawer 104 (e.g., two tracks on opposite sides of the support frame 106 for each drawer 104).

The support frame 106 and the door 108 of cabinet housing 102 may be manufactured from bended sheet metal that is welded together at the corners and are typically made of one or more materials, including stainless steel and titanium. The hinges 110 and the tracks 112 of the cabinet housing 102 are typically made of one or more materials, such as stainless steel or titanium. With the door 108 closed shut against the support frame 106, the cabinet housing 102 typically has a length of about 45.7 cm to about 50.8 cm (e.g., about 48.3 cm), a width of about 45.7 cm to about 50.8 cm (e.g., about 48.3 cm), and a height of about 72.2 cm to about 80.2 cm (e.g., about 76.2 cm). Each wall of the double-wall construction of the cabinet housing 102 typically has a wall thickness of about 0.23 cm to about 0.26 cm (e.g., about 0.25 cm), and the walls are typically spaced apart from each other by about 0.93 cm to about 1.03 cm (e.g., about 0.98 cm). A vacuum pressure is present between the walls of the double-wall construction to provide insulation to an interior region of the drawer 104. Since a vacuum has a very low rate of heat transfer, the vacuum pressure between the double walls minimizes heat transfer due to convection and conduction.

Figure 4:
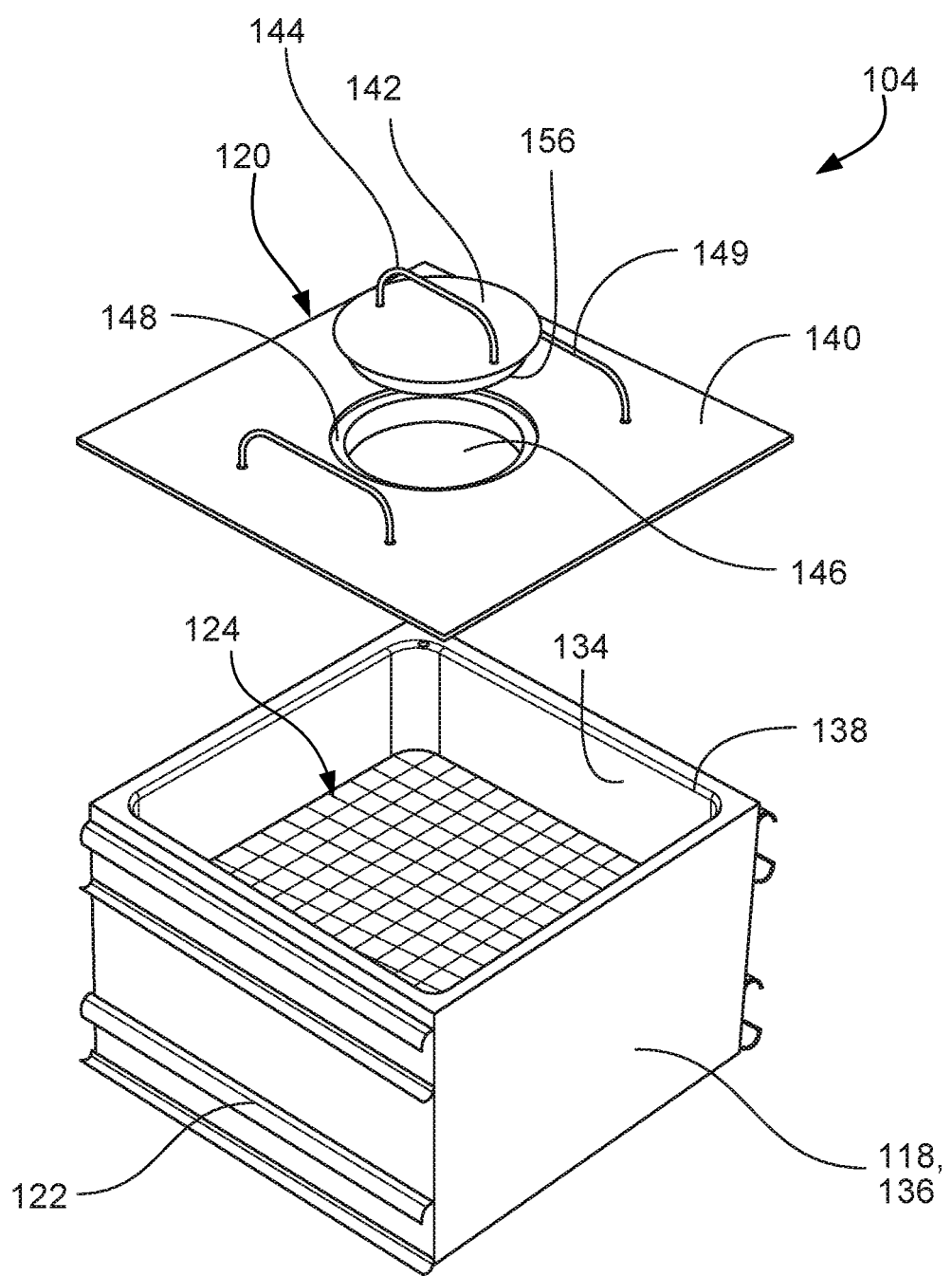
FIG. 4 is an exploded, perspective view of the drawer of the storage system of FIG. 1.
Figure 5:
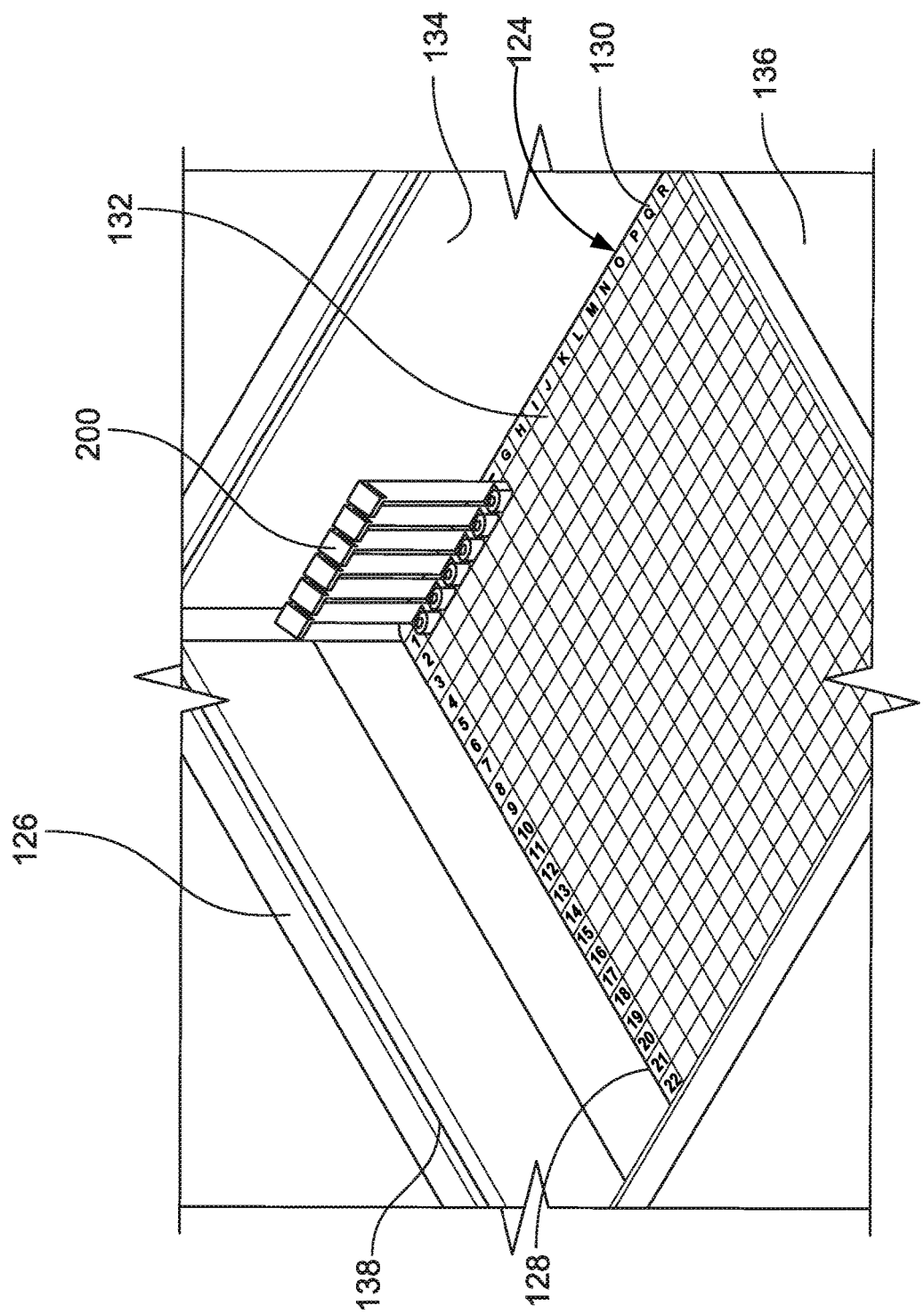
FIG. 5 is a perspective zoom view of an interior region of the drawer of FIG. 4.

Referring to FIGS. 3-5, the drawers 104 are slidable in and out of the support frame 106 along the tracks 112. Each drawer 104 includes a container 118, a lid 120, and multiple tracks 122 disposed along opposite sides of the container 118. The container 118 is designed to hold a low temperature substance in which cryostorage carriers 200 can be submerged, as will be discussed in more detail below with respect to FIG. 10. The container 118 has a generally rectangular shape and is formed from a double wall that is defined by an interior surface 134 and an exterior surface 136. The container 118 defines a seat 138 (e.g., a recessed surface) adjacent a top surface 126 on which the lid 120 can rest to close the container 118. The container 118 includes a support grid 124 (e.g., a multi-well structure) that is positioned below the top surface 126.

Figure 6:
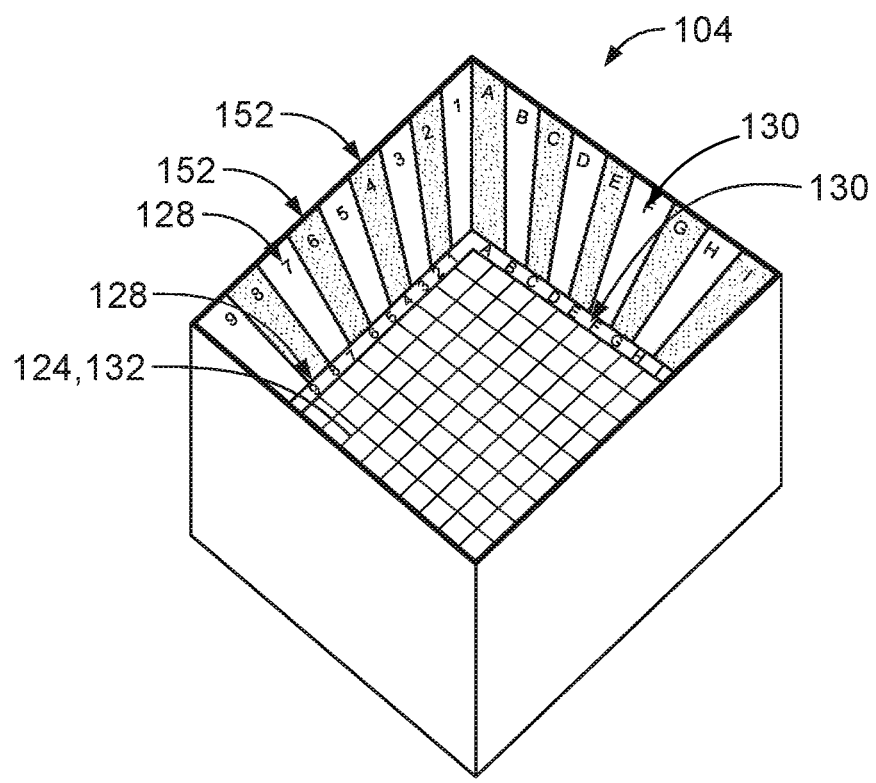
FIG. 6 is a perspective view of an interior region of the drawer of FIG. 4, illustrating alphanumeric labels and shading.
Figure 7:
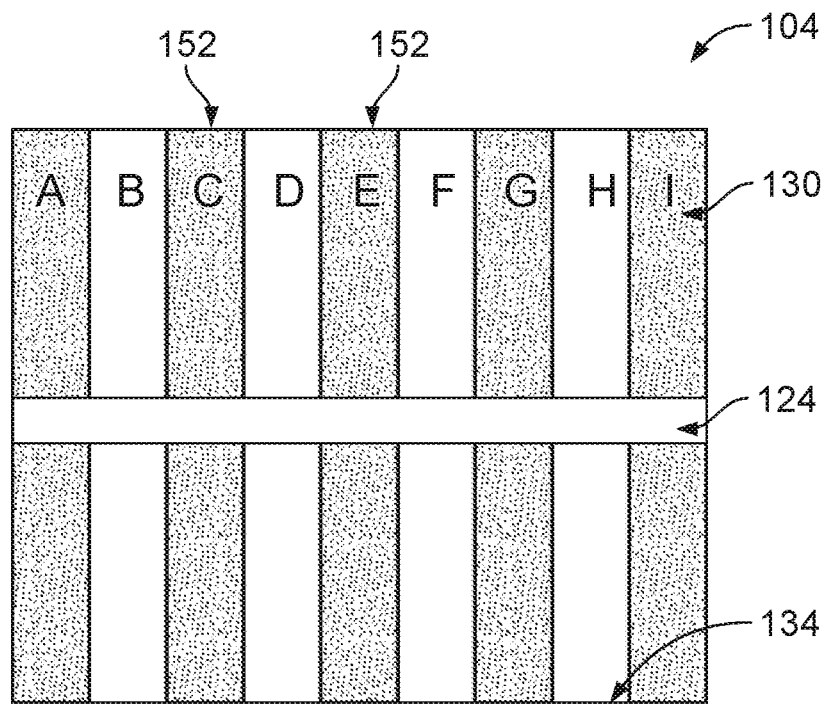
FIG. 7 is a side view of the interior region of the drawer of FIG. 6.

Referring to FIGS. 6 and 7, the support grid 124 includes two, opposite rows of numerical labels 128 and two, opposite rows of alphabet labels 130 that are disposed along edges of the support grid 124. The container 118 also includes two corresponding rows of numerical labels 128 and two corresponding rows of alphabetical labels 130 that are disposed along the interior surface 134 and remain visible in case the low temperature substance should cover a top surface of the support grid 124. The numerical labels 128 and the alphabetical labels 130 together identify multiple storage receptacles 132 of the support grid 124. For example, each storage receptacle 132 can be identified in association with one number and one letter. Additionally, alternating shaded columns 152 are disposed along the interior surface 134 of the container 118 in association with alternating alphanumeric labels 128, 130 to facilitate visual identification of the storage receptacles 132. The storage receptacles 132 are generally rectangular (e.g., square) in cross-sectional shape and are sized to hold respective cryostorage devices 200. Each drawer 104 typically includes 625 to 729 storage receptacles 132 (e.g., depending on a size of the storage receptacles 132, a wall thickness of the support grid 124, and other size parameters of the drawer 104), such that the total storage capacity of the storage system 100 is 1250 to 1458 cryostorage carriers 200.

The lid 120 has a substantially square outer profile and includes an insert 154 that is designed to rest atop the seat 138 of the container 118 to close the container 118. While the lid 120 can close the container 118, the lid 120 does not hermetically seal the container 118. As a result, the low temperature substance can undergo expansion without dislodging or damaging the lid 120. The lid 120 includes a cover 140, a cap 142 that can be used to open and close the cover 140, a handle 144 attached to the cap 142, and two handles 149 attached to the cover 140. The cover 140 defines an opening 146 through which the low temperature substance can be delivered to (e.g., poured into) the container 118. The opening 146 is surrounded by a recessed surface 148, through which an insert 156 of the cap 142 passes to close the opening 146.

Figure 8:
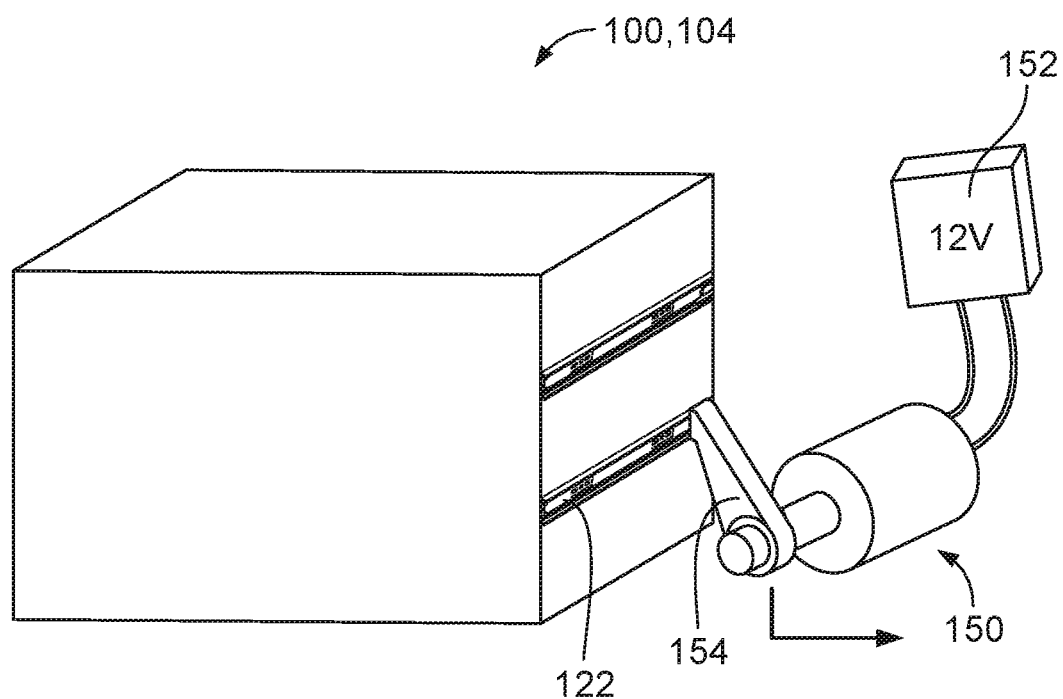
FIG. 8 is a perspective view of a portion of the storage system of FIG. 1, including the drawer and an associated linear actuator.

Referring to FIG. 8, each drawer 104 can manually slide or automatically slide in and out of the support frame 106 of the cabinet housing 102 along the tracks 112, 122. Automatic movement of the drawers 104 can be advantageous, given a heavy combined weight (e.g., of the container 118, the low temperature substance disposed therein, and the cryostorage devices 200 carried therein) that would have to be overcome for manual movement of the drawer 104. For example, the storage system 100 includes multiple linear actuators 150 that are respectively associated with the tracks 122 along the container 118 (e.g., one linear actuator per set of two tracks 122). Each linear actuator 150 is attached to a power supply 152 (e.g., mounted to a rear portion of the support frame 106) on one end and a rigid member 154 (e.g., a rigid bar) on a second end. The rigid member 154 is attached to the track 122 such that when the linear actuator 150 extends, the drawer 104 slides forward (e.g., out of the support frame 106) in a fluid manner along the tracks 112. The drawer 104 can be manually slid out of the support frame 106 using a handle 162.

Components of the drawer 104 are made of one or more materials that can mechanically and chemically withstand low temperatures for an extended period of time (e.g., at least about 40 years), such as titanium or stainless steel. Components of the drawer 104 may be manufactured from bended sheet or machined metal. The container 118 of the drawer 104 typically has a total length of about 45.7 cm to about 50.7 cm (e.g., about 48.2 cm), a total width of about 40.9 cm to about 45.5 cm (e.g., about 43.2 cm), and a total height of about 29.4 cm to about 32.6 cm (e.g., about 31.0 cm). Each wall of the double-wall construction of the container 118 typically has a wall thickness of about 0.24 cm to about 0.26 cm (e.g., about 0.25 cm), and the walls are typically spaced apart from each other by about 1.92 cm to about 2.14 cm (e.g., about 2.03 cm). A vacuum pressure is present between the walls of the double-wall construction, thereby minimizing heat transfer due to convection and conduction.

An interior region of the container 118 (e.g., defined by the interior surface 134) typically has a length of about 36.1 cm to about 40.1 cm (e.g., about 38.1 cm), a width of about 36.6 cm to about 40.6 cm (e.g., about 38.6 cm), and a height of about 24.8 cm to about 27.6 cm (e.g., about 26.2 cm). The storage receptacles 132 typically have a length of about 1.16 cm to about 1.28 cm (e.g., about 1.22 cm) and width of about 1.16 cm to about 1.28 cm (e.g., about 1.22 cm). The support grid 124 typically has a vertical length of about 0.24 cm to about 0.27 cm (e.g., about 2.54 cm) and is positioned at a height (e.g., determining the height of the storage receptacles 132) of about 9.02 cm to about 10.03 cm (e.g., about 9.53 cm) above a bottom interior surface 134 of the container 118. Walls of the support grid 124 typically have a thickness of about 0.17 cm to about 0.19 cm (e.g., about 0.18 cm). The labels 128, 130 may be applied to the interior surface 134 of the container 118 and to the support grid 124 via various manufacturing techniques, such as laser marking, etching, or engraving.

The lid 120 of the container 118 has a total length and a total width that are about equal to those of the container 118. The lid 120 has a double-wall construction for insulation. The walls of the lid 120 have a thickness of about 0.24 cm to about 0.27 cm. A spacing between the walls of the lid 120 is about 0.757 cm to about 0.842 cm. The insert 154 of the lid 120 typically has a length of about 36.09 cm to about 40.10 cm (e.g., about 38.1 cm), a width of about 36.09 cm to about 40.10 cm (e.g., about 38.1 cm), and a depth of about 2.16 cm to about 2.39 cm (e.g., about 2.29 cm), according to a size of the seat 138 of the container 118. The recessed surface 148 of the cover 140 and the cap 142 typically have an outer diameter of about 16.84 cm to about 18.71 cm (e.g., about 17.78 cm). The insert 156 of the cap 156 typically has a depth of about 2.16 cm to about 2.41 cm (e.g., about 2.29 cm) and a diameter of about 14.44 cm to about 16.04 cm (e.g., about 15.24 cm), according to a diameter of the opening 146 in the cover 140 of the lid 120.

Figure 9:
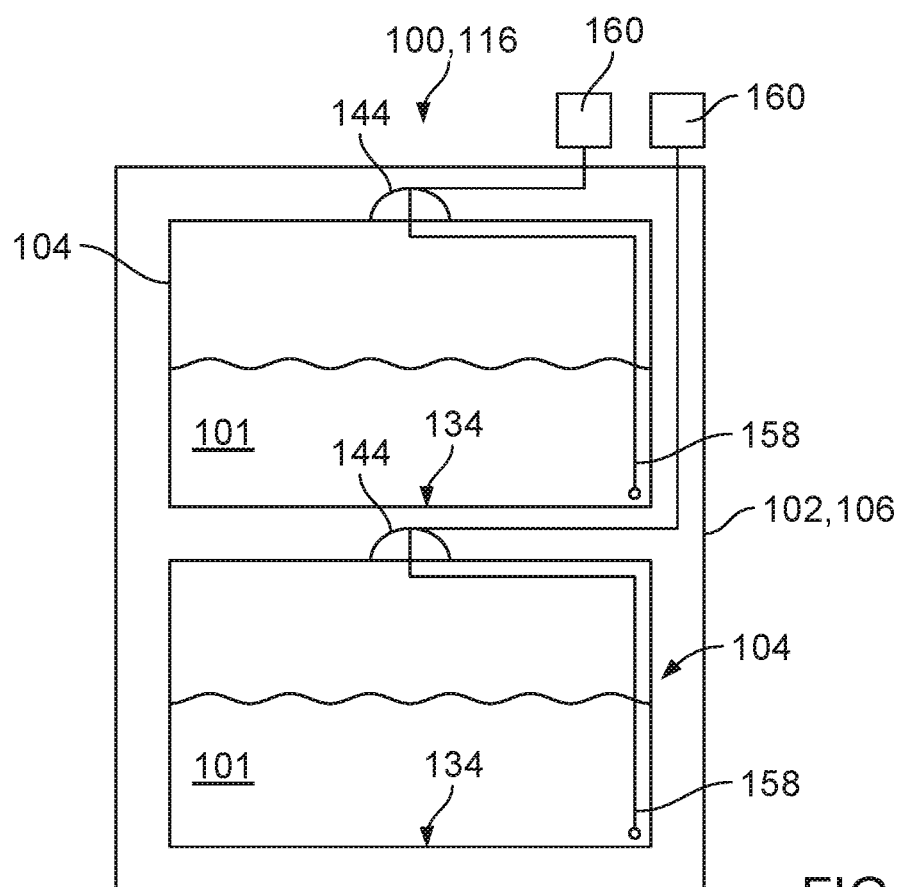
FIG. 9 is a cross-sectional schematic side view of the storage system of FIG. 1, illustrating a sensor system integrated with the cabinet housing and the drawers.

Referring to FIG. 9, the sensor system 116 of the storage system 100 includes a level sensor 158 and an associated alarm 160 for each drawer 104. The alarms 160 may be battery powered and are positioned along an upper portion of the support frame 106 of the cabinet housing 102. The level sensors 158 extend from the alarms 160 downward through the cabinet housing 102 and through the lids 120 of the drawers 104 to bottom interior surfaces 134 of the containers 118. The interior region of the container 118 is typically about 40% to about 60% filled with a low temperature substance 101, such that the low temperature substance 101 fills the container 118 to a height of about 12 cm to about 20 cm above a bottom interior surface 134 of the container 118. The alarms 160 and the level sensors 158 are programmed to detect a drop in a level of the low temperature substance 101 (e.g., due to evaporation) below a threshold value (e.g., about 40% to about 45% volume of the interior region of the container 118), to emit one or both of an audio sound alert or a visual light alert upon such detection, and to terminate the alert once the substance level has been replenished above the threshold value.

During use of the storage system 100, the door 108 is opened from the support frame 106 of the cabinet housing 102 to allow access to the drawers 104 (refer to FIG. 2). The drawers can be slid out automatically via the linear actuators 150 or by hand using the handle 162 (refer to FIG. 2). The lid 120 of the drawer 104 is removed from the container 118 to deposit or retrieve one or more cryostorage devices 200 or to replenish the low temperature substance within the container 118 (refer to FIG. 3). The cryostorage carrier 200 can be easily identified via the support grid 124 and the alphanumeric labels 128, 130 (refer to FIGS. 5-7). The low temperature substance can also be replenished by removing the cap 142 of the lid to expose the opening 146 of the lid (refer to FIG. 4) to the interior region of the container 118. A user can be notified to replenish the low temperature substance when one of the alarms 160 of the storage system 100 emits an audio alert or a visual alert (refer to FIG. 9).

The storage system 100 provides several advantages with respect to conventional low temperature specimen storage apparatuses. For example, the storage system 100 provides a storage capacity that scales with the number of drawers 104 arranged in the stacked configuration within the cabinet housing 102 such that the storage system 100 optimally uses vertical space while minimizing horizontal space. Therefore, a capacity of the storage system 100 to store cryostorage carriers 200 (e.g., the number of drawers 104 multiplied by the number of storage receptacles 132 included within each drawer 104) is not limited by a footprint of the storage system 100. In this regard, a storage capacity of the storage system 100 can be about 5-10 times greater than that of other low temperature specimen storage apparatuses that have similar footprints. Furthermore, the rectangular (e.g., square) shape of the footprint of the cabinet housing 102 maximizes a use of floor space for a given footprint length and width. Additionally, the multi-well design of the support grid 124 (e.g., including the storage receptacles 132, the alphanumeric labels 128, 130, and the shaded columns 152) provides a two-dimensional, organized manner of storing the cryostorage carriers 200 in an easy-to-use and easy-to-identify manner that reduces the risk of patient or sample misidentification.

Figure 10:
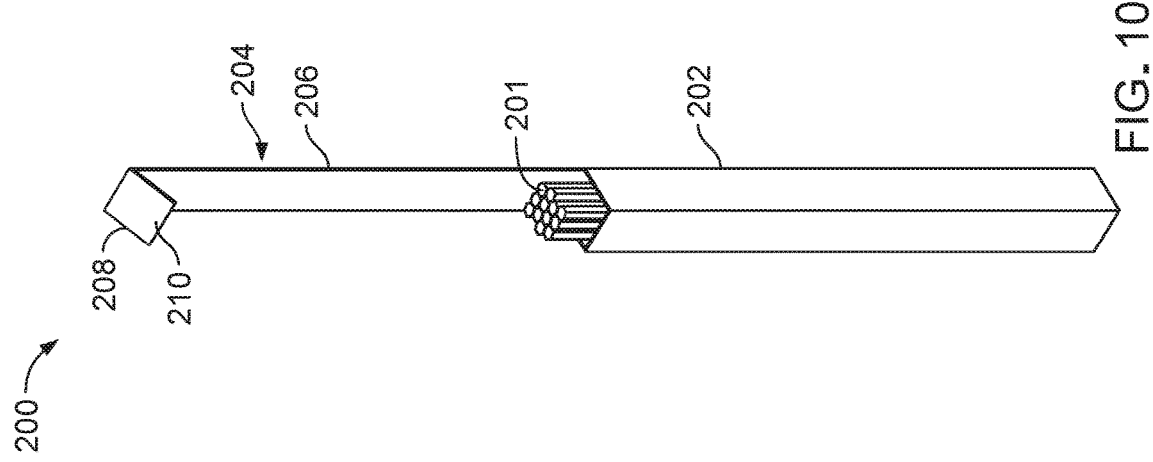
FIG. 10 is a perspective view of a cryostorage carrier that can be stored in the storage system of FIG. 1.

FIG. 10 illustrates a perspective view of one of the cryostorage carriers 200. The cryostorage carrier 200 is designed to hold multiple elongate, tubular cryopreservation devices 201 for storage of the cryopreservation devices 201 (e.g., and the specimens contained therein) within a low temperature substance. For example, the cryostorage carrier 200 is sized to fit within a receptacle 132 of the drawer 104 (or within a storage area of another storage system). The multi-tube carrying capacity of the cryostorage carrier 200 enables grouped storage of multiple cryopreservation devices 201 carrying specimens from the same patient or family, thereby reducing a risk of specimen misidentification.

The cryostorage carrier 200 includes a container 202 and a stem 204 that extends from the container 202. The container 202 is an open, elongate structure that has a carrying capacity of 10 to 12 cryopreservation devices 201. The stem 204 includes an extension portion 206 and a handle 208 that is oriented at an acute angle with respect to the extension portion 206 to facilitate grasping of the handle 208. The extension portion 206 heightens the handle 208 above the container 202 and above a surrounding storage receptacle 132 for easy access to and manipulation of the cryostorage carrier 200. A length of the extension portion 206 also allows for deep submersion of the cryostorage carrier 200 within the low temperature substance to ensure that the specimens contained within the cryopreservation devices 201 are sufficiently exposed to the low temperature sub stance.

The handle 208 may be grasped directly by hand or using a tool that is specifically designed to grasp the cryostorage carrier 200. The handle 208 provides a large surface 210 on which human-readable information can be written or printed or on which a label (e.g., a tag or a sticker) including machine-readable information can be adhered. Example labels include radio frequency identification (RFID) labels, barcode labels, and quick response (QR) code labels. Example information includes one or more of patient information, sample identification information, and storage parameter information.

The container 202 has a rectangular (e.g., square) cross-sectional shape. The container 202 typically has a length of about 1.08 cm to about 1.19 cm (e.g., about 1.14 cm), a width of about 1.08 cm to about 1.19 cm (e.g., about 1.14 cm), and a height of about 11.43 cm to about 12.70 cm (e.g., about 12.07 cm), such that the container 202 surrounds a majority of the surface area of the cryopreservation devices 201 and a majority of the surface area of the container 202 is submerged in the low temperature substance within a surrounding storage receptacle 132. The extension portion of the stem 204 typically has a length of about 10.15 cm to about 11.28 cm (e.g., about 10.72 cm) and a width of about 1.08 cm to about 1.19 cm (e.g., about 1.14 cm). The handle 208 of the stem 204 typically has a length of about 1.03 cm to about 1.14 cm (e.g., about 1.09 cm) and a width of about 1.08 cm to about 1.19 cm (e.g., about 1.14 cm). The cryostorage carrier 200 typically has a wall thickness of about 0.028 cm to about 0.032 cm (e.g., about 0.03 cm).

The cryostorage carrier 200 is made of one or more materials that can mechanically and chemically withstand low temperatures for an extended period of time (e.g., at least about 40 years), such as polypropylene, polyethylene, or polycarbonate. The cryostorage carrier 200 may be manufactured via injection molding.

While certain embodiments have been described above, other embodiments are possible.

Figure 11:
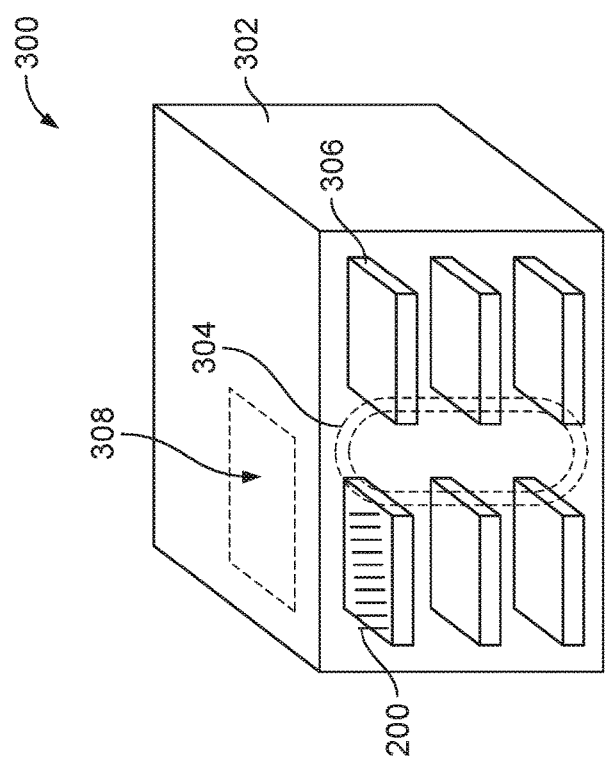
FIG. 11 is a perspective view of a low temperature storage system having a cryostorage carrier tray assembly with a ferris-wheel type construction.

For example, FIG. 11 illustrates a storage system 300 that has a tray assembly having a ferris wheel-type construction (e.g., a rotating component with multiple carriers). The storage system 300 includes a housing 302, a rotating component 304 disposed within the housing 302, and multiple trays 306 that are connected to and move with the rotating component 304. The housing 302 has a double-wall construction and includes a cap 308 that provides access to the trays 306.

The rotating component 304 is an elongate structure that has a vertical orientation that provides for optimal use of a vertical space of the housing 302. The storage system 300 further includes a motor and a manual crank by which the rotating component 304 can be actuated automatically and manually, respectively. For example, the rotating component 304 can be rotated to place a desired tray 306 adjacent the cap 308 or adjacent a side opening in the housing 302 so that the tray 306 can be accessed to deliver cryostorage carriers (e.g., the cryostorage carriers 200) to the tray 306 or to retrieve cryostorage carriers stored in the tray 306. A vertical configuration of the rotating component 304 also optimizes floor space occupied by the footprint of the housing 302, and the separate spacing of the trays 306 along the rotating component 304 facilitates organization of the cryostorage carriers 200 within the housing 302.

In some embodiments, the trays 306 are substantially similar in construction and function to the drawers 104 (e.g., including one or both of a container 118 and a lid 102), but without the tracks 122. In alternative embodiments, the trays 306 have a different construction. The low temperature substance is held within each of the trays 306.

The cabinet housing 302 may be manufactured from bended sheet metal that is welded together at the corners and is typically made of one or more materials, including stainless steel and titanium. The cabinet housing 302 typically has a length of about 45.75 cm to about 50.84 cm (e.g., about 48.3 cm), a width of about 45.75 cm to about 50.84 cm (e.g., about 48.3 cm), and a height of about 72.19 cm to about 80.21 cm (e.g., about 76.2 cm). Each wall of the double-wall construction of the cabinet housing 302 typically has a wall thickness of about 0.236 cm to about 0.263 cm (e.g., about 0.25 cm), and the walls are typically spaced apart from each other by about 0.93 cm to about 1.03 cm (e.g., about 0.98 cm). The rotating component 304 typically has a height of about 40.92 cm to about 45.47 cm (e.g., about 43.2 cm) and a width of about 9.18 cm to about 10.21 cm (e.g., about 9.7 cm).

Figure 12:
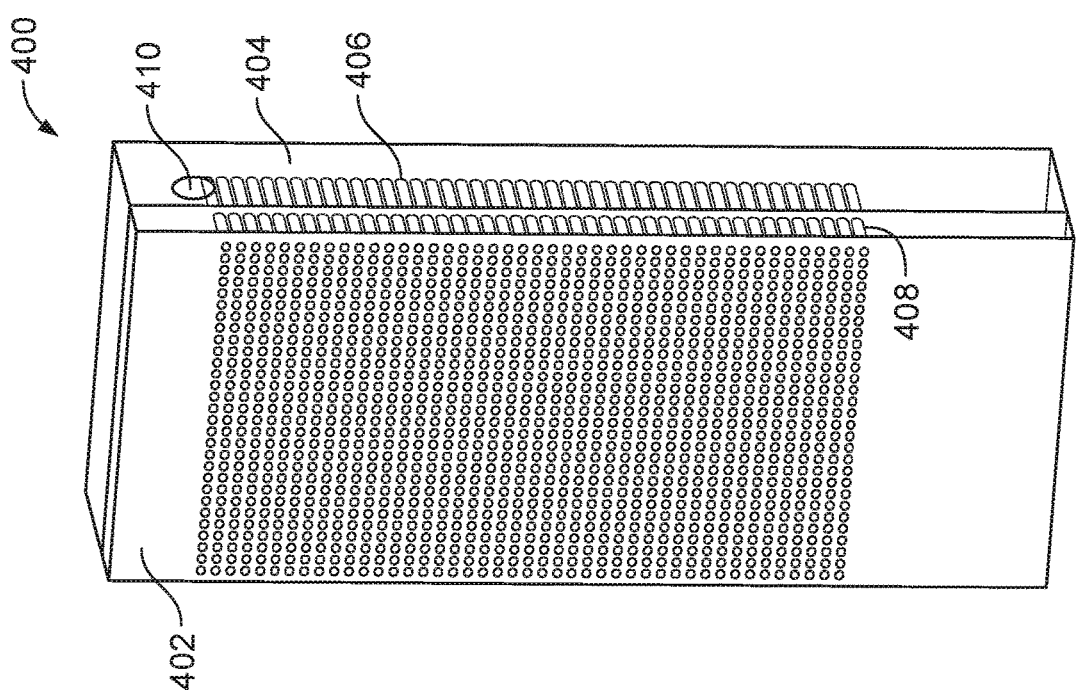
FIG. 12 is a perspective view of a low temperature storage system with an upright shelving configuration.

FIG. 12 illustrates a storage system 400 that has a two-part upright construction. For example, the storage system 400 includes a front housing 402 and a rear housing 404 that have double-wall constructions. The rear housing 404 can be filled with a low temperature substance via an access port 410 and defines multiple receptacles 406 in which cryostorage carriers (e.g., the cryostorage carriers 200) or cryopreservation devices (e.g., the cryopreservation devices 201) can be stored adjacent the low temperature substance. The front housing 402 defines multiple slots 408 that respectively correspond to the receptacles 406 and provide passageways through which the cryostorage carriers or cryopreservation devices can be inserted and removed. The low temperature substance is not in contact with the cryopreservation devices 201. Rather, the low temperature substance fills the rear housing 404. The slots 408 together form a grid (e.g., including alphanumeric labels) by which the cryostorage carriers or cryopreservation devices can be identified. A depth of the rear housing can be as short as that allowed to carry the cryostorage carriers or cryopreservation devices, such that an upright orientation of the storage system 400 provides a minimal footprint.

The storage system 400 typically includes 1300 to 1400 receptacles 406 and slots 408. The housings 402, 404 may be manufactured from bended sheet metal that is welded together at the corners and is typically made of one or more materials, including titanium or stainless steel. The housings 402, 404 typically have a height of about 144.4 cm to about 160.4 cm (e.g., about 152.4 cm) and a width of about 45.8 cm to about 50.8 cm (e.g., about 48.3 cm). The rear housing 404 typically has a depth of about 22.9 cm to about 25.5 cm (e.g., about 24.2 cm), and the front housing 402 typically has a depth of about 11.5 cm to about 12.7 cm (e.g., about 12.1 cm). Each wall of the double-wall construction of the housings 402, 404 typically has a wall thickness of about 0.24 cm to about 0.26 cm (e.g., about 0.25 cm), and the walls are typically spaced apart from each other by about 0.93 cm to about 1.03 cm (e.g., about 0.98 cm).

Figure 13:
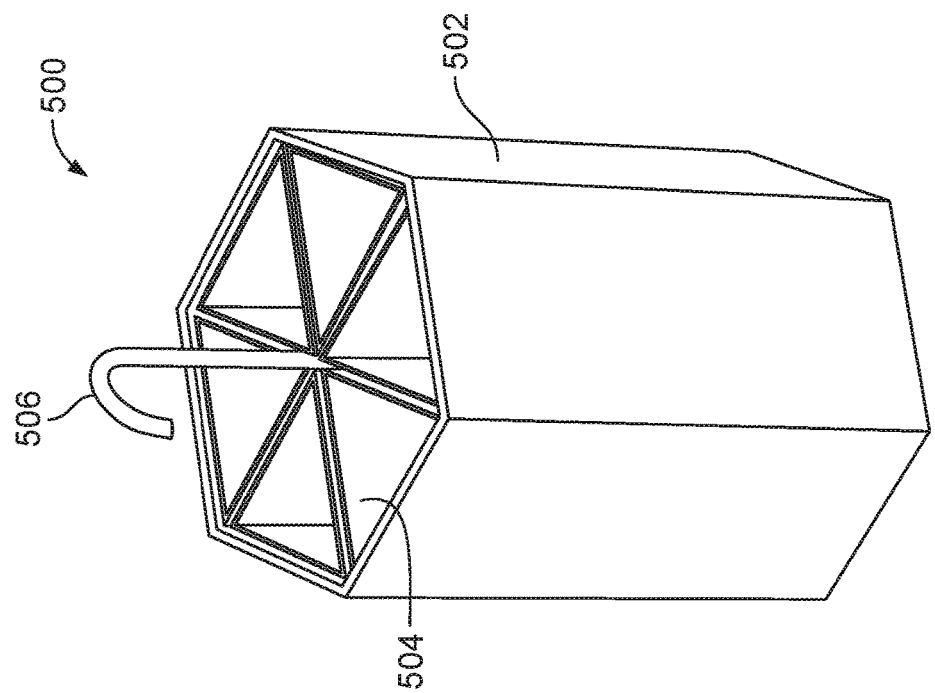
FIG. 13 is a perspective view of a hexagonal cryostorage carrier.

FIG. 13 illustrates a cryostorage carrier 500 that can store cryostorage carriers (e.g., the cryostorage carriers 200) or cryopreservation devices (e.g., the cryopreservation devices 201) within a storage system holding a low temperature substance. The cryostorage carrier 500 includes a container 502 with a hexagonal cross-sectional shape, multiple (e.g., six) divider sections 504 disposed within the container 502, and a handle 506 (e.g., a hook) that extends from the container 502. The divider sections 504 have a triangular cross-sectional shape and therefore fit together to fill the shape of the container 502. The divider sections 504 also have distinct colors to facilitate identification of cryostorage carriers or cryopreservation devices contained therein.

The container 502 and the divider sections 504 may be manufactured from bended sheet metal that is welded together at the corners and are typically made of one or more materials, including stainless steel or titanium. The container 502 and the divider sections 504 typically have a height of about 11.5 cm to about 12.7 cm (e.g., about 12.1 cm) and a wall thickness of about 0.24 cm to about 0.26 cm (e.g., about 0.25 cm). The container 502 typically has a width of about 9.09 cm to about 10.1 cm (e.g., about 9.6 cm), and the divider sections 504 typically have a width of about 0.24 cm to about 0.26 cm (e.g., about 0.25 cm).

While the above-discussed storage systems and cryostorage carriers have been described as including certain dimensions, sizes, shapes, and materials, in some embodiments, storage systems and cryostorage devices that are substantially similar in structure and function to the above-discussed embodiments may include different dimensions, sizes, shapes, and materials.

What is claimed is:

1. A low temperature storage system, comprising:
   a cabinet housing; and
   a drawer that is slidable in and out of the cabinet housing, the drawer comprising:
      an interior wall and an exterior wall defining an insulated space therebetween,
      a support grid disposed within an interior region defined by the interior wall of the drawer, the support grid defining multiple receptacles arranged in a matrix configuration and respectively sized to receive a storage carrier,
      first markings and second markings printed on the drawer in a manner such that any one of the first markings and any one of the second markings together correspond to one of the multiple receptacles arranged in the matrix configuration, and
      a lid configured to close the interior region, the lid comprising:
         a cover defining an opening through which a fluid can be delivered to the interior region, and
         a cap configured to close the opening.

2. The low temperature storage system of claim 1, wherein the first markings and the second markings comprise alphanumeric labels.

3. The low temperature storage system of claim 1, wherein the first markings and the second markings are printed on the support grid.

4. The low temperature storage system of claim 1, wherein the first markings and the second markings are printed on the interior wall.

5. The low temperature storage system of claim 4, wherein the drawer further comprises shaded columnar marks disposed along the interior wall.

6. The low temperature storage system of claim 1, wherein the multiple receptacles comprise 1200 to 1500 receptacles.

7. The low temperature storage system of claim 1, wherein each of the multiple receptacles has a length of about 1.1 cm to about 1.2 cm and a width of about 1.1 cm to about 1.2 cm.

8. The low temperature storage system of claim 1, wherein the multiple receptacles have a rectangular cross-sectional shape.

9. The low temperature storage system of claim 1, wherein the interior wall and the exterior wall comprise titanium.

10. The low temperature storage system of claim 1, wherein the insulated space comprises a vacuum pressure.

11. The low temperature storage system of claim 1, wherein the drawer is configured to hold a fluid having a temperature of about −196° C. or less within the interior region.

12. The low temperature storage system of claim 11, further comprising a level sensor that is configured to detect a level of the fluid.

13. The low temperature storage system of claim 12, further comprising an alarm that is configured to emit an alert when a level of the fluid falls below a threshold level.

14. The low temperature storage system of claim 1, wherein the drawer is a first drawer, the low temperature storage system further comprising a second drawer that is slidable in and out of the cabinet housing.

15. The low temperature storage system of claim 14, wherein the first and second drawers are arranged in a stacked vertical configuration within the cabinet housing.

16. The low temperature storage system of claim 1, further comprising the storage carrier.

17. The low temperature storage system of claim 16, wherein the storage carrier comprises a rectangular receptacle sized to fit within each of the multiple receptacles of the support grid and to carry a plurality of cryopreservation devices.

18. The low temperature storage system of claim 17, wherein the storage carrier comprises a handle that extends from the rectangular receptacle.

19. The low temperature storage system of claim 1, wherein the interior wall is a first interior wall, wherein the exterior wall is a first exterior wall, wherein the insulated space is a first insulated space, and wherein the cabinet housing comprises a second interior wall and a second exterior wall defining a second insulated space therebetween.

20. The low temperature storage system of claim 1, wherein the insulated space is a first insulated space, and wherein the lid further comprises a first wall and a second wall defining a second insulated space therebetween.

21. A low temperature storage container, comprising:
an interior wall and an exterior wall defining an insulated space therebetween;
a support grid disposed within an interior region defined by the interior wall, the support grid defining multiple receptacles arranged in a matrix configuration and respectively sized to receive a storage carrier;
first markings and second markings printed on the low temperature storage container in a manner such that any one of the first markings and any one of the second markings together correspond to one of the multiple receptacles arranged in the matrix configuration; and
a lid configured to close the interior region, the lid comprising:
a cover defining an opening through which a fluid can be delivered to the interior region, and
a cap configured to close the opening.

22. The low temperature storage container of claim 21, wherein the first markings and the second markings comprise alphanumeric labels.

23. The low temperature storage container of claim 21, wherein the first markings and the second markings are printed on the support grid.

24. The low temperature storage container of claim 21, wherein the first markings and the second markings are printed on the interior wall.

25. The low temperature storage container of claim 24, wherein the low temperature storage container further comprises shaded columnar marks disposed along the interior wall.

26. The low temperature storage container of claim 21, wherein the multiple receptacles comprise 600 to 800 receptacles.

27. The low temperature storage container of claim 21, wherein each of the multiple receptacles has a length of about 1.1 cm to about 1.2 cm and a width of about 1.1 cm to about 1.2 cm.

28. The low temperature storage container of claim 21, wherein the multiple receptacles have a rectangular cross-sectional shape.

29. The low temperature storage container of claim 21, wherein the interior wall and the exterior wall comprise titanium.

30. The low temperature storage container of claim 21, wherein the insulated space comprises a vacuum pressure.

31. The low temperature storage container of claim 21, wherein the low temperature storage container is configured to hold a fluid having a temperature of about −196° C. or less within the interior region.

32. The low temperature storage container of claim 21, wherein the insulated space is a first insulated space, and wherein the lid further comprises a first wall and a second wall defining a second insulated space therebetween.

* * * * *

UNITED STATES PATENT AND TRADEMARK OFFICE
CERTIFICATE OF CORRECTION

PATENT NO. : 10,451,340 B2  
APPLICATION NO. : 15/840268  
DATED : October 22, 2019  
INVENTOR(S) : Aabha Bharat Gami et al.

Page 1 of 1

It is certified that error appears in the above-identified patent and that said Letters Patent is hereby corrected as shown below:

On the Title Page

Column 2 (Attorney, Agent, or Firm), delete "Ricahrdson" and insert -- Richardson --

Signed and Sealed this
Twenty-fourth Day of December, 2019

Andrei Iancu
*Director of the United States Patent and Trademark Office*